United States Patent [19]

Vercellotti et al.

[11] 4,009,463
[45] Feb. 22, 1977

[54] ACOUSTIC EMISSION MONITORING SYSTEM

[75] Inventors: Leonard C. Vercellotti, Verona; Perry J. Hite, Sr., Murrysville, both of Pa.

[73] Assignee: Westinghouse Electric Corporation, Pittsburgh, Pa.

[22] Filed: Mar. 13, 1975

[21] Appl. No.: 558,107

[52] U.S. Cl. .............................. 340/16 R; 73/67; 73/88 R
[51] Int. Cl.² .......................................... G01S 5/18
[58] Field of Search .............. 340/6 R, 16 R; 73/67, 73/88.3

[56] References Cited
UNITED STATES PATENTS 3,504,334   3/1970   Turnage, Jr. ................... 340/16 R

OTHER PUBLICATIONS

Schofield, "Utilization of Acoustic Emission for In-Service Inspection," *Instn. Mech. Engrs.*, 1972.

*Primary Examiner*—Richard A. Farley
*Attorney, Agent, or Firm*—D. C. Abeles; Z. L. Dermer

[57] ABSTRACT

Methods and apparatus for identifying the source location of acoustic emissions generated within or on an acoustically conductive medium segregated into a plurality of quadrilateral monitoring zones. A plurality of acoustic receivers are communicably coupled to the surface of the medium respectively at the zone corner locations. Each receiver is responsive to the reception of an acoustic emission to provide a corresponding electrical output. The electrical response of the respective receivers are coupled to corresponding counters in a manner to enable the counters to sequence through their respective counting states. The receiver outputs are monitored to identify the first zone exhibiting an acoustic reception at all four corners. Once such a zone has been identified, all counters are inhibited from sequencing and are locked into the last counting state cycled. Preferably, the counter associated with the last receiver within the identified zone monitoring the acoustic event is locked in the zero counting state as a reference origin for the algebraic operations (more commonly known as triangulation) conventionally used to map the source location of acoustic emissions.

Desirably, the electronics of the apparatus of this invention are arranged in modular form with interlocks adaptable to be connected to corresponding interlocks on like modules to accommodate expansion of the system to handle an infinite number of zones.

19 Claims, 8 Drawing Figures

ACOUSTIC EMISSION MONITORING SYSTEM

BACKGROUND OF THE INVENTION

This invention pertains generally to methods and apparatus for monitoring acoustic emissions, and more particularly to methods and apparatus that identify the source location of such emissions.

Non-destructive methods for testing mechanical components and metal formations formed during the manufacture of such components, such as weld seams, have been employed for a number of years to detect discontinuities that might otherwise affect the reliability of operating components. If it were not for such inspection techniques, flaws could result in mal-functions during use, which are likely to cause substantial and sometimes irreparable damage.

In recent years, acoustic inspection techniques have been developed which have significantly advanced the state of the art. Usually such techniques employ ultrasonic technology in various embodiments that basically rely on externally generated acoustic pulses which are transmitted within the member being inspected. The time of travel of reflected signals are interpreted to identify the presence and the location of flaws. The application of ultrasonic non-destructive testing techniques, however, usually requires elaborate scanning arrangements which are costly and are not normally practical for on-line applications.

Acoustic emission monitoring techniques have also been employed in non-destructive testing applications, however, such procedures have encountered great difficulties in identifying the source locations of flaws in varying geometries of materials. Additionally, such procedures have proved highly susceptable to multiple acoustic emissions occurring within the same time frame that obscure identification of the source location of any particular emission.

The invention described in application Serial No. 556,354, filed Mar. 7, 1975 entitled "Acoustic Emission Monitoring System" by D. M. Romrell addresses many of the problems encountered in applying acoustic emission monitoring techniques as a non-destructive tool for testing weldments. While the invention described in the cited application significantly advances the present state of the art in an application to relatively small identifiable areas of inspection, the procedures and apparatus set forth become cumbersome and expensive when applied to monitoring relatively large surface areas where the zones of suspected flaw formation are not specifically identifiable.

Presently, fault location using acoustic sensors is being pursued as a means of detecting incipient faults in the pressure walls of reactor vessels. While the sensors and signal conditioners are critical components in obtaining dependable performance, the deployment of sensors and the amount of circuitry required to determine fault location are also important considerations. Since acoustic signals in large medias such as reactor pressure vessels are attenuated and protrusions obstruct propagation through some regions, a large number of sensors is needed, for expansive regions such as are encountered on a reactor pressure vessel, without general duplication of functions.

Accordingly, an acoustic monitoring system is desired that will facilitate on-line monitoring of operating components and discriminate against multiple acoustic events. Additionally, such a system is desired that can be expanded with a minimal of circuitry and cost to accommodate an infinite number of sensors in an application to relatively large surface areas.

SUMMARY OF THE INVENTION

Briefly, this invention provides methods and apparatus for identifying the source location of acoustic emissions generated within or on an acoustically conductive medium. The apparatus and methods of this invention divide the medium being monitored into a plurality of quadrilateral zones. Each corner of the respective zones are monitored for the reception of acoustic emissions. Each reception enables a corresponding counter to sequence through its respective counting states. The zone first encountering the reception of an acoustic emission at all four monitoring locations is identified and its corresponding counters are locked in the last state exhibited at the moment the last monitoring location within the identified zone responds to the emission. The outputs of the counters are then available for triangulation to pinpoint the source location of the emission.

In the preferred embodiment, each zone shares two corners with an adjacent zone to minimize the number of transducers required, and preferably, all counters are stopped from sequencing when a particular zone is identified as monitoring an acoustic reception at all four of its monitoring locations.

Desirably, in accordance with this invention, the counter, logic and transmission circuitry is designed in one module having interlocks connectable to like interlocks on similar modules for expansion of the system to accommodate an infinite number of zones with a minimum of components. Expansion in this manner enables large surface areas to be monitored at minimal expense without compromising the quality of the results obtained or increasing the cost of the analytical components employed in interpreting the counter outputs to identify the location of a particular emission. Inasmuch as only one zone is identified at a time corresponding to the area from which the emission was generated, only one analytical unit is required, regardless of the number of zones the system is expanded to accommodate.

BRIEF DESCRIPTION OF THE DRAWINGS

For a better understanding of the invention, reference may be had to the preferred embodiment, exemplary of the invention, shown in the accompanying drawings, in which.

DESCRIPTION OF THE PREFERRED EMBODIMENT

Fault location using acoustic sensors has been pursued in the past and is presently being explored as a means of detecting incipient faults in the pressure walls of reactor vessels. While a large amount of development work has been done in the areas of sensors, and signal conditioners to accommodate the critical conditions experienced in a nuclear environment, to obtain dependable performance, the deployment of sensors and the amount of circuitry required to determine fault location are important considerations that have not significantly been developed to date to accommodate the surveillance of relatively large surface areas as are encountered on a reactor pressure vessel. Since acoustic signals are attenuated and protrusions obstruct propagation through some regions, a large number of sensors are needed to accommodate such applications. Expansion of existing apparatus and methods employed in typical applications only results in duplication of functions and equipment that can increase the probability of malfunction and the overall cost of such systems. Accordingly, it is the object of this invention to minimize the logic circuitry required per sensor, the number of sensors needed and the computer capability required to perform arithmetic operations for location of the origin of an acoustic emission.

Generally, three sensors can be used to determine the origin of an acoustic emission on a surface. A fourth sensor is necessary to resolve ambiguities associated with the sign of a quadratic which shows up in the explicit solution of the fault coordinates as can be appreciated from the following explanation.

Figure 2:
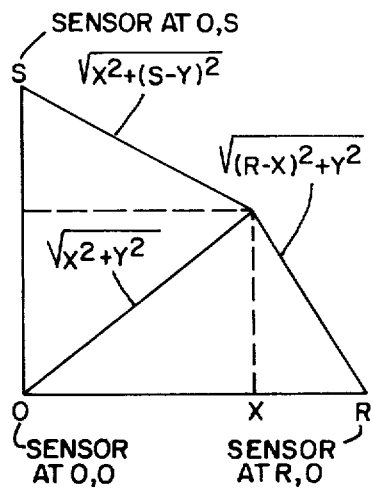
FIG. 2 is a graphic derivation of an explicit solution for fault location from the time of arrival differences obtained in accordance with this invention.

For the purpose of explanation, assume rectangular coordinates can be employed in the triangulation operation, with one sensor positioned at the origin and two others placed at distances R and S respectively as shown in FIG. 2. While the locus of all points with constant difference in times of arrival between any two sensors is a hyperbola, the solution for the intersection of the two hyperbolas can be found explicity through the following straight forward derivation.

The propagation velocity in the material is assumed to be $v$. Also, if the difference in time of arrival of an emission from $x, y$ at O, O and R, O is $\Delta t_1$, then the difference in distance traversed is $v\Delta t_1$. Therefore, it can be appreciated from FIG. 2 that:

$$\sqrt{x^2 + y^2} = \sqrt{(R-x)^2} + v\Delta t_1 \quad (1)$$

Similarly, if the difference in times of arrival of an emission from $x, y$ at O, O and O, S is $\Delta t_2$, then the difference in distance traversed is $v\Delta t_2$. Therefore, $$\sqrt{x^2 + y^2} = \sqrt{x^2 + (S-y)^2} + v\Delta t_2 \quad (2)$$

Let $v\Delta t_1 = \Delta d_1$ and $v\Delta t_2 \, \Delta d_2$; then:

$$-\Delta d_1 + \sqrt{x^2 + y^2} = \sqrt{(R-x)^2 + y^2}. \quad (3)$$

Squaring both sides of the equation gives $$\Delta d_1^2 - 2\Delta d_1 \sqrt{x^2 + y^2} + x^2 + y^2 = R^2 - 2Rx + x^2 + y^2. \quad (4)$$

Simplifying gives $$\Delta d_1^2 - 2\Delta d_1 \sqrt{x^2 + y^2} = R^2 - 2Rx. \quad (5)$$

Solving for $\sqrt{x^2 + y^2}$ yields $$\sqrt{x^2 + y^2} = -\frac{(R^2 - 2Rx - \Delta d_1^2)}{2\Delta d_1}. \quad (6)$$

Similarly it can be shown that $$\sqrt{x^2 + y^2} = -\frac{(S^2 - 2Sy - \Delta d_2^2)}{2\Delta d_2}. \quad (7)$$

Equating (6) and (7)

$$R^2 - 2Rx - \Delta d_1^2 = \frac{\Delta d_1}{\Delta d_2}(S^2 - 2Sy - \Delta d_2^2). \quad (8)$$

or $$x = \frac{1}{2R}\left[R^2 - \Delta d_1^2 - \frac{\Delta d_1}{\Delta d_2}S^2 + \Delta d_1 \Delta d_2 + \frac{2\Delta d_1}{\Delta d_2}S_y\right] \quad (9)$$

Equation (9) is of the form $$x = k + ly \quad (10)$$

where $k = R^2 - \Delta d_1^2 - \frac{\Delta d_1}{\Delta d_2}S^2 + \Delta d_1 \Delta d_2$ and $l = \frac{\Delta d_1}{\Delta d_2} \frac{S}{R}$.

Substituting $x = k + ly$ in Eq. (6) and squaring both sides.

$$(k + ly)^2 + y^2 = \left(\frac{R^2 - 2Rk - 2Rly - \Delta d_1^2}{2\Delta d_1}\right)^2 \quad (11)$$

Then $$k^2 + 2kly + l^2y^2 + y^2 = m^2 + 2mny + n^2y^2 \quad (12)$$

where $m = \frac{R^2 - 2Rk - \Delta d_1^2}{2\Delta d_1}$ and $n = -\frac{Rl}{\Delta d_1}$.

Rewriting (12) gives a quadratic equation in $y$ $$y^2(l^2 + 1 - n^2) + 2(kl - mn)y + (k^2 - m^2) = 0 \quad (13)$$

Solving (13) using the quadratic formula results in $$y = \frac{-2(kl - mn) \pm \sqrt{4(kl - mn)^2 - 4(l^2 + 1 - n^2)(k^2 - m^2)}}{2(l^2 + 1 - n^2)} \quad (14)$$

which is an explicit solution of $y$ in terms of known constants and the times of arrival.

Figure 3:
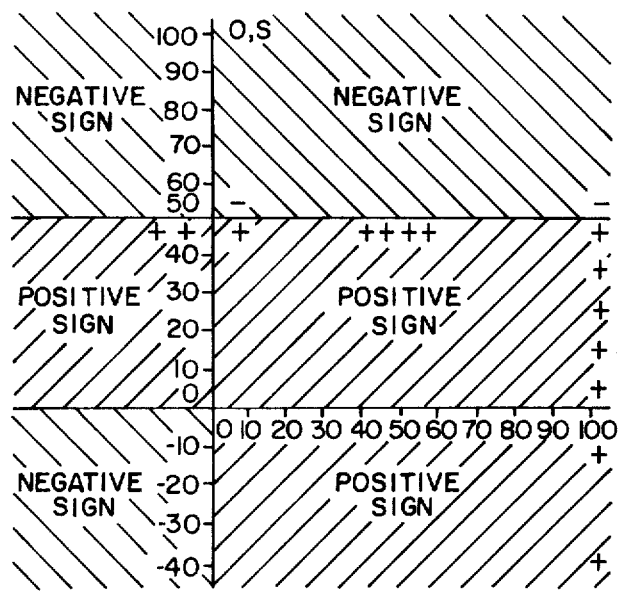
FIG. 3 is a graphic illustration of the quadratic formula sign for various regions defined by the sensor placement of this invention.

Once $y$ is known, $x$ is found from the linear expression of equation (10). The only question is the sign to be used in the quadratic formula for equation (14). FIG. 3 shows the sign of the quadratic term as it applies to the various regions with respect to sensors located at O, O; R, O; and O, S respectively. No simple rule based on the sign of the difference in time of arrival is apparent. For faults known to lie in the area of y greater than 0, the rule is simply use the opposite sign of $\Delta t_2$. Since faults cannot be restricted in a practical system, a fourth sensor at R, S can be used with the sensors at R, O and O, S to perform a second triangulation using the sign of the quadratic applicable for the region of y less than S. Agreement of the result of this second triangulation to the result of the first triangulation resolves the ambiguity and identifies faults in the range of y greater than or equal to O and less than or equal to S for all x. Errors in location for faults outside the region surrounded by the sensors do become more serious depending on the resolution of the time measurement which can be obtained. Therefore, each region should be served by its own set of sensors with triangulation taking place for the first group of sensors to detect the acoustic burst.

Since both $\Delta d_1$ and $\Delta d_2$ show up in the denominators of the terms to be calculated, a zero difference in times of arrival needs to be recognized to prevent division by zero. Upon detection, a small number providing insignificant error can be added to the time of arrival to prevent overflow.

Thus, in accordance with this invention, the acoustically conductive medium to be monitored is divided into a plurality of quadrilateral zones with sensors positioned at the corners of the respective zones to monitor the reception of acoustic emissions so that the time difference in reception at the respective monitored locations can be determined for the triangulation calculations. Desirably, as illustratively shown in FIG. 1A, adjacent zones share sensors to minimize the numer of components required in the system.

Figure 1A:
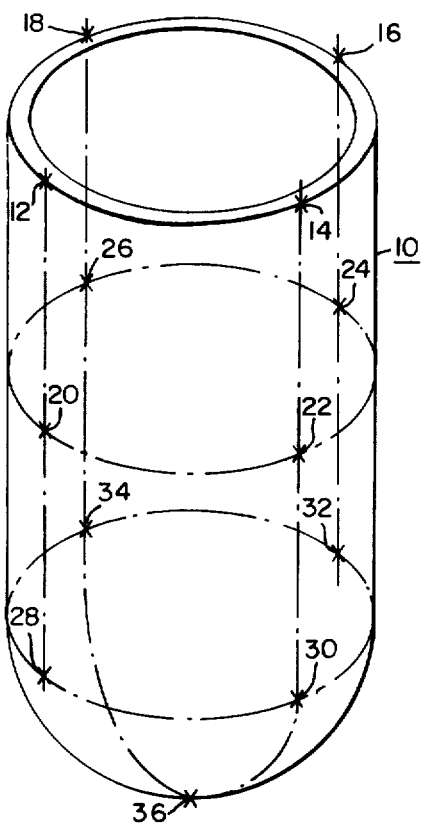
FIG. 1A is a schematic illustration exemplary of a typical arrangement of sensors on a reactor vessel.
Figure 1B:
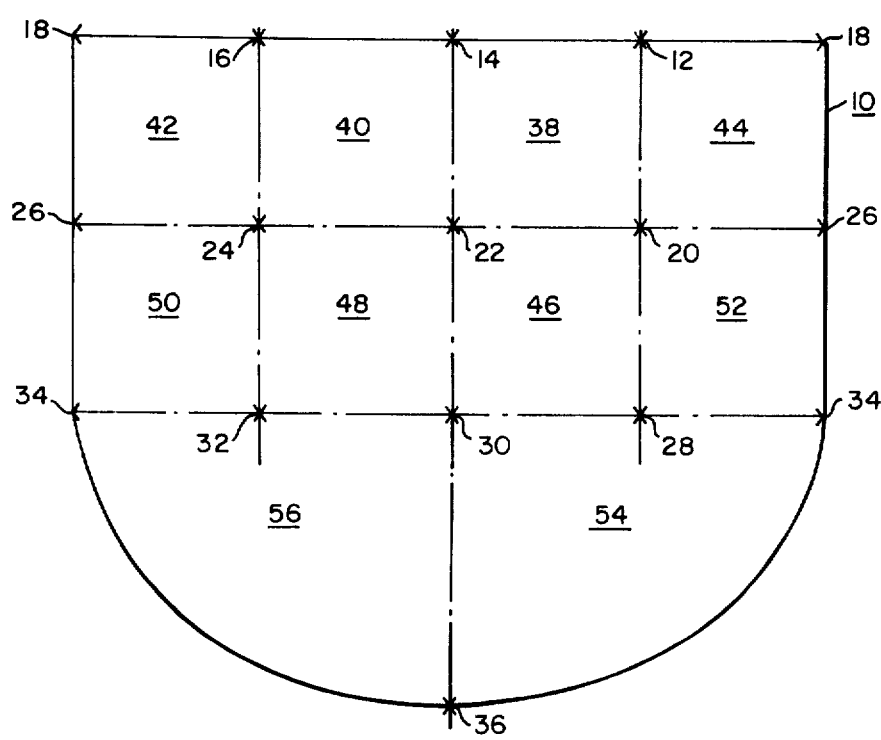
FIG. 1B is a plan development of FIG. 1A.

Referring to FIG. 1B, which is a planned development of FIG. 1A, it can be appreciated that a schematic representation of a reactor vessel 10 is provided segregated into eight generally rectangular zones 38 through 52 with the lower hemispherical portion of the vessel divided into two separate zones 54 and 56, respectively defined by sensors 28, 30, 34 and 36, and 30, 32, 34 and 36. There, the two zones defining the hemispherical portion of the vessel share three sensors 30, 34 and 36. Similarly, twelve sensors, 12 through 34, define the remaining eight zones 38 through 52 with each sensor being shared between two to four zones. Accordingly, a minimum of equipment is required to monitor the entire vessel. This is particularly true where generally round (i.e. circular to elliptical) surfaces are to be monitored where the zones can be coupled around the entire periphery of the surface. While quadrilateral zones defined by the sensor positions are preferred, it can be appreciated from the illustrative geometry shown in FIG. 1 that generally rectangular zones, though providing a maximum sharing of sensors and therefore desirable, are not a necessary limitation of this invention. Accordingly, quadrilateral is employed to define any four-sided zone such as the bi-hemispherical portion 54 defined by the sides connecting sensors 30–36, 36–34, 34–28 and 28–30. Thus, the zone configuration will depend upon the geometry of the surface being monitored.

Figure 4:
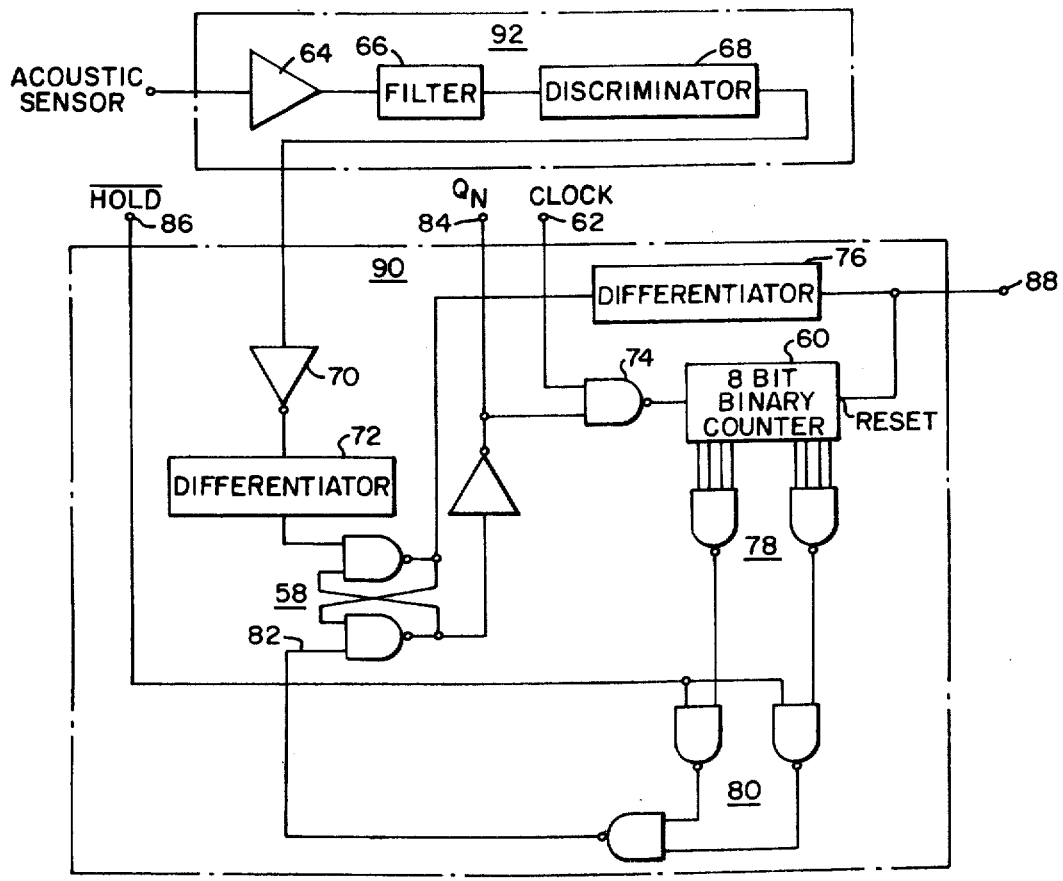
FIG. 4 is a block diagram of the per sensor circuitry of this invention.

The differences in times of arrival of acoustic emissions at the sensor locations can be established by communicating the respective sensor outputs to corresponding set-reset flip-flop and counter circuitry. A block diagram of the per sensor circuitry illustrative of the preferred embodiment of this invention is illustrated in FIG. 4. An acoustic emission burst will set the flip-flop 58, reset the counter 60 and allow pulses from a reference clock supplied to terminals 62 to be accumulated by the counter. When pulses are received at all four sensors of a particular zone, the four corresponding flip-flops 58 will be set, the counter contents will be held and the computer, which is employed to perform the triangulation calculations, will be signaled that the counters are ready to be read. The computer will then read the particular counters which have been responsible for interrupting the computer and determine the differences in times of arrival of the acoustic emissions at the four sensor locations. From the time of arrival information the x, y coordinates are calculated using the equations developed previously. The computer will then release the $\overline{\text{HOLD}}$ signal which has been locking up the contents of the counters, reset the flip-flops and allow the circuitry to monitor the next acoustic emission burst.

More specifically, the outputs of the respective acoustic sensors are communicated to a series of signal conditioners 64, 66 and 68 which respectively amplify the sensor output, filter extraneous noise, communicate only signals above a predetermined level to avoid extraneous outputs and provide a pulse stretching operation. The output of the level detector 68 is inverted by the logic component 70 and communicated to a differentiator 72 which is responsive to the leading edge of the signal to set the flip-flop 58. The differentiator is supplied to assure that lengthy acoustic sensor outputs do not interfere with reset signals applied to the flip-flop at terminal 82. A differentiator 76 is responsive to the initiation of the setting of the flip-flop 58 to reset the counter 60. The counter is cycled by an externally generated clock pulse communicated through terminal 62 and NAND gate 74 when the flip-flop 58 is set. The set condition of the flip-flop, identified at terminal 84, is communicated to an additional monitoring circuit that is employed to indicate the first zone exhibiting a reception on all four of its corresponding sensors. As previously explained, when four sensors associated with a particular zone indicate the reception of an acoustic event, a $\overline{\text{HOLD}}$ signal is applied at terminal 86 to the logic gates 80 which supply a reset signal through terminal 82 to the flip-flop 58. The reset signal prevents the clock 62 from further sequencing the counter 60 and maintains the last counter state exhibited prior to the application of the $\overline{\text{HOLD}}$ signal. A signal corresponding to the $\overline{\text{HOLD}}$ signal is applied to terminal 88 to prevent the counter 60 from resetting until the computer has had an opportunity to read the appropriate counter states corresponding to the sensors associated with the zone that indicated a response at all four monitoring locations. The logic circuitry 78 monitors the counter output and is responsive to the counters maximum counter state to enable logic gates 80 to communicate a reset signal to terminal 82 of the control flip-flop 58; disconnecting the clock input at NAND gate 74 to prevent the counter from further sequencing through its respective states.

Noise can also trip the discriminator output module 68 and set the flip-flop 58. Each counter, therefore, is allowed to count to its maximum value, which is preferably determined by the time required to traverse the largest distance between sensors of a particular zone (in this particular example a diagonal on the sensor array) and then reset its corresponding control flip-flop 58 through the maximum count decoder 78 and logic circuitry 80. This allows up to three of the four sensor outputs to occur during the maximum time of arrival difference interval without triangulation being registered. The effect of a large electrical disturbance is more frequently the setting of all four flip-flops and the reading of zero difference in times of arrival at all sensors. This condition, however, can be readily rejected by the computer and the flip-flops reset to accept the next acoustic emission burst.

Figure 5:
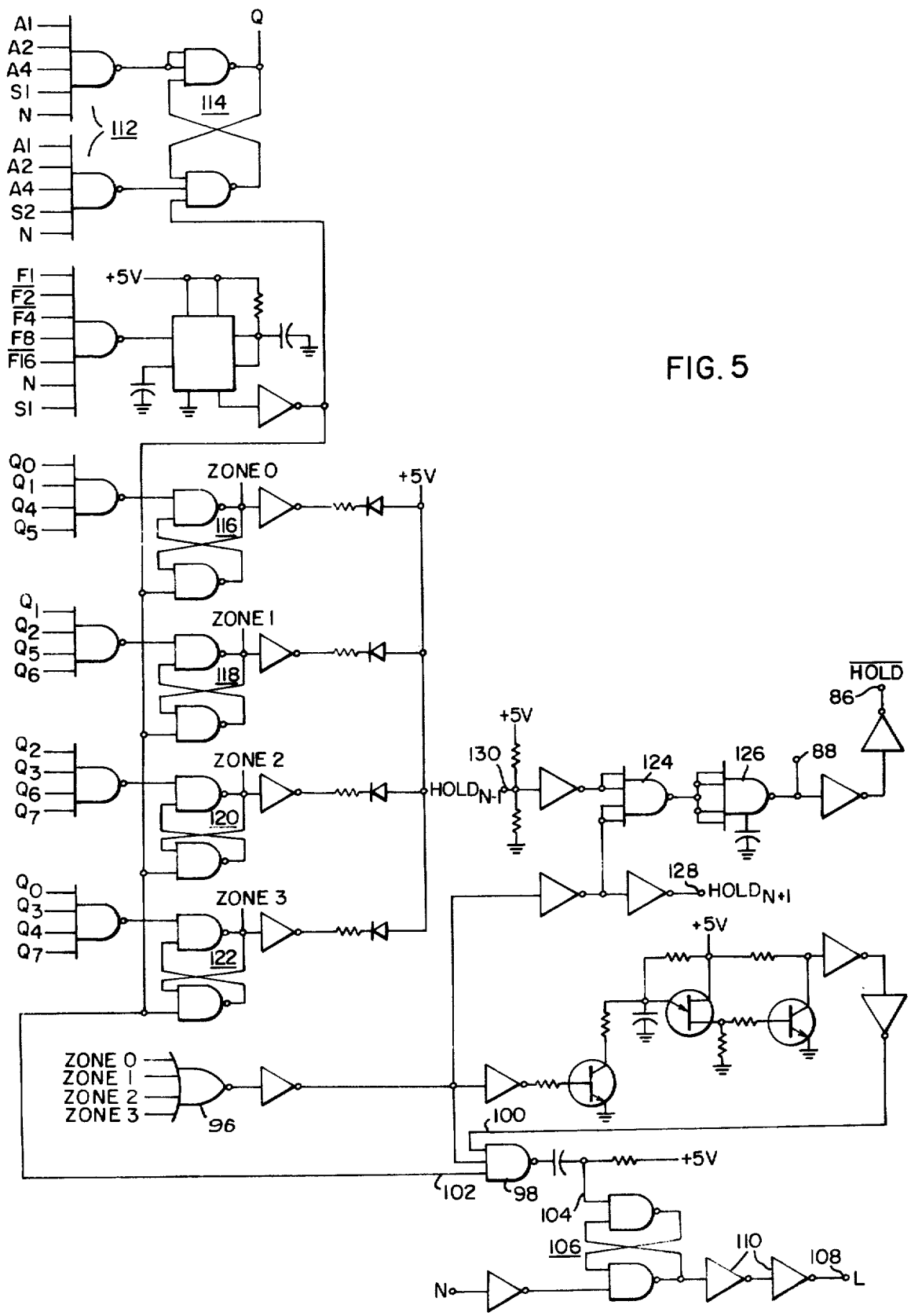
FIG. 5, is a schematic of the interface circuitry for the triangulation module of this invention.
Figure 6:
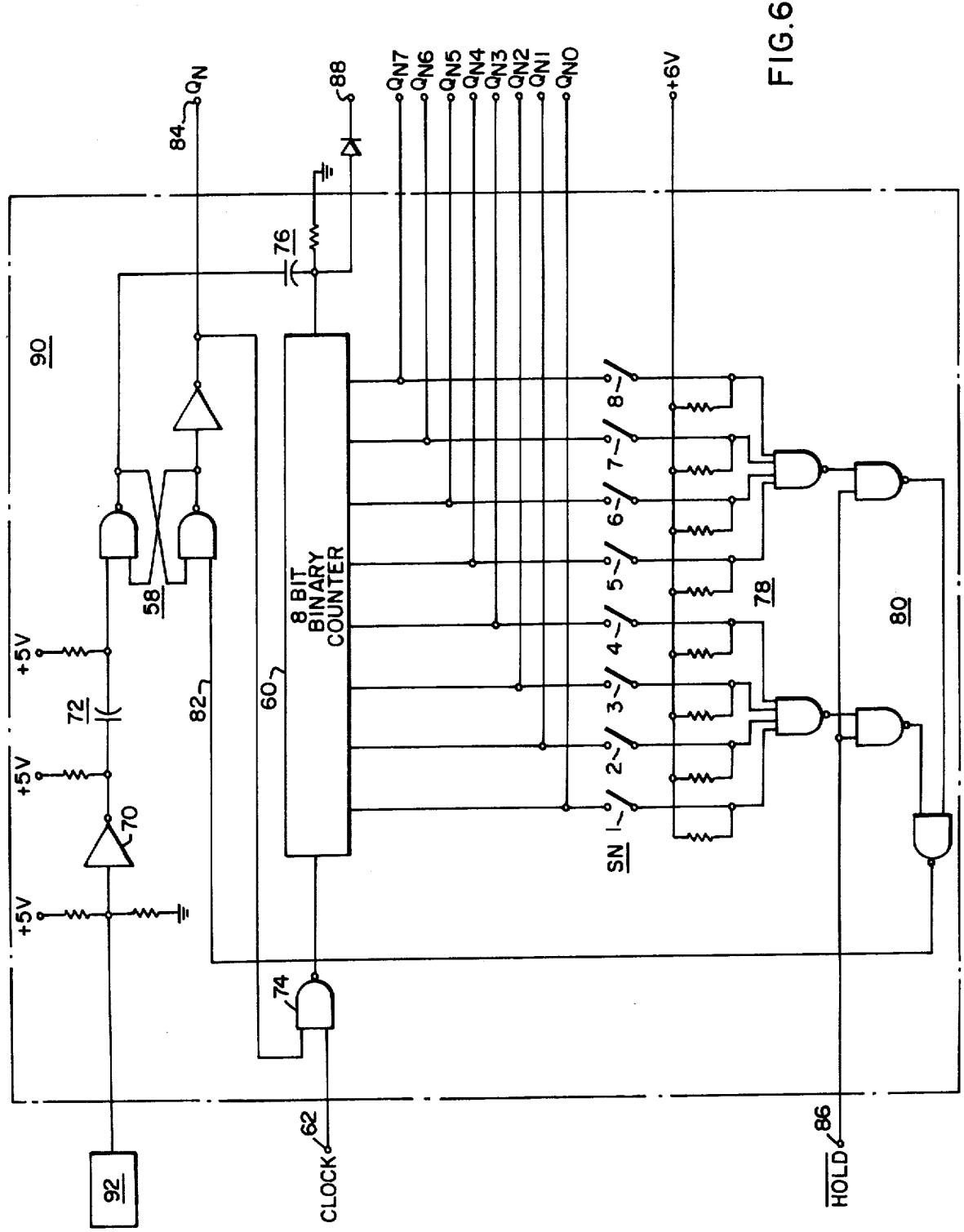
FIG. 6 is a circuitry schematic of the counter circuitry of the triangulation module of this invention.
Figure 7:
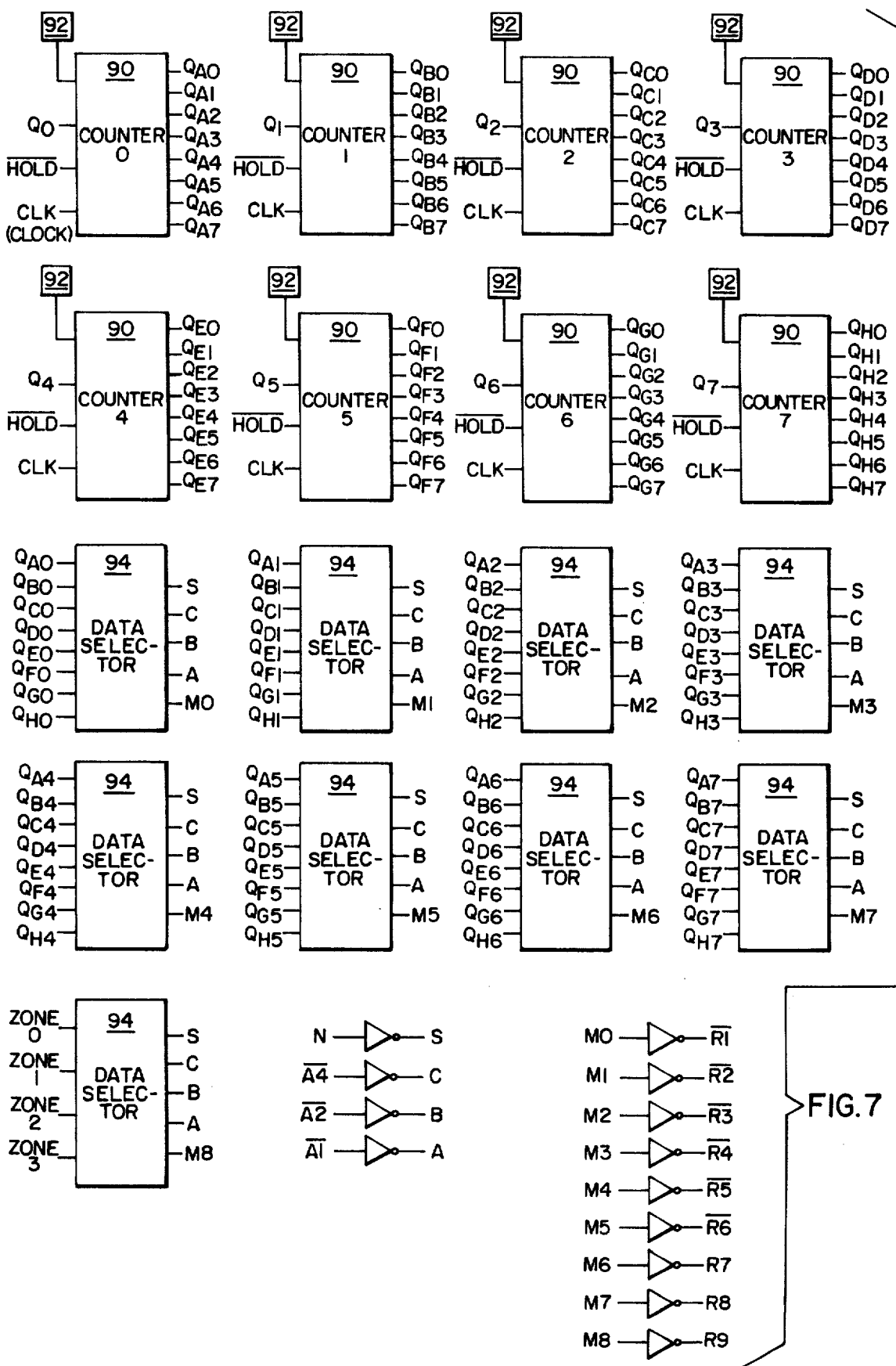
FIG. 7 is a circuitry schematic of the data selector portion of the triangulation module of this invention.

The schematic for the triangulation circuitry that interfaces with the computer is shown in FIGS. 5, 6 and 7. The triangulation circuitry is divided into modules with each module containing circuitry for eight time of arrival counters (illustrated in FIG. 7 by counter circuit arrangements 90) as well as interface circuitry to and from a CAMAC data way. The logic employed in the illustrated exemplary embodiment includes diode-transistor logic (DTL) and complementary-symmetry metal oxide-semiconductor (COS/MOS) devices. The corresponding outputs of the counter circuitry arrangements 90, represented in the block diagram of FIG. 4 and the schematic of FIG. 6 as $Q_N$, are respectively identified in FIG. 7 by $Q_0$ through $Q_7$. Similarly, the sensor outputs from the signal conditioning circuitry 92 illustrated in block form in FIG. 4 and generally identified in FIG. 6 as $I_N$, are respectively noted in FIG. 7 by reference characters $I_0$ through $I_7$. The eight bit counter associated with each sensor input can be implemented using a CD 4040 COS/MOS integrated circuit. The maximum count from each counter output is selectable by rocker type switches identified by reference character SN in FIG. 6 and is decoded by two four-input CD 4012 COS/MOS NAND gates. The gate outputs combine with the HOLD signal as previously explained to determine when the control flip-flop 58 is to be reset. When the control flip-flop 58 is set, it enables the clock pulses supplied through terminals 62 to be registered in the counter. The outputs from the 8 bit counters can be read on the computer in sequence by implementing, for example, SN74LS151 data selectors identified by reference character 94 in FIG. 7.

The outputs from the counters are read by a minicomputer via a CAMAC dataway interface. The acronym CAMAC relates to a governmental agency approved standard for digitally monitored and controlled nuclear instrumentation. The standard describes modules in a crate or cage which in turn are controlled by a master module termed a crate controller. Data in digital form can be sent to or read from the modules by dataway bus lines generally manufactured into the back of the module panels. Sub-address codes, functional codes, and strobe inputs are sent from the controller to perform particular functions in each module. Interrupt and response signals are generated by the modules to advise the controller that an operation is complete and data is ready to be read. The controller in turn utilizes another interface system termed a "branch highway" to communicate with a processor such as the mini-computer.

The dataway commands used by the triangulation module are listed in the following table:

TABLE I

DATAWAY FUNCTIONS USED BY TRIANGULATION MODULE

| Signal | Functional Description |
| --- | --- |
| N | Station Number: selects the module. |
| A1 | |
| A2 | |
| | Sub-Address: selects a section of the module. |
| A4 | |
| A8 | |
| F1 | |
| F2 | |
| F4 | Function Codes: defines the function to be performed in the module. |
| F8 | |
| F16 | |
| S1 | Strobe 1: controls first phase of operation. |
| S2 | Strobe 2: controls second phase of operation. |
| L | Look-at-me (interrupt): indicates request for service. |
| Q | Response: indicates status of a feature selected by command. |
| X | Command Accepted: module is able to perform action required by the command. |
| R1-R9 | Data Lines: carry information from/to the module. |

The input commands to the triangulation module from the controller are station number N, sub-address codes A1, A2, A4, A8, function codes F1, F2, F4, F8, F16 and the two strobes S1 and S2. The N command selects the module as to location in the crate. The sub-address commands A1, A2, A4, A8 select a section of the module, and functions F1, F2, F4, F8, F16 define the function to be performed in the module. The strobe signals S1, and S2 control the timing sequence during a command operation.

The signals generated within the triangulation module to be sent to the controller are the status signals: L (interrupt or look at me), Q (response), and X (command accepted). In the schematics of the triangulation module shown in FIGS. 5, 6 and 7, the circuitry for the N command, sub-address commands A1, A2, A4, A8, the function commands F1, F2, F4, F8, F16, and their respective complements are shown.

Interrupt operation occurs when the module sends the look at me L to the controller as a request for service. This occurs when any one of four zones, zone 0, 1, 2, or 3, is set to a logic one. Four zones are described inasmuch as, as previously explained, each module is set up to handle eight sensors. A particular zone is selected when its four associated control flip-flops are all set to logical ones. Zone zero gets selected when control flip-flop outputs Q0, Q1, Q4, and Q5 are set to ones by a pulse at the respective sensor inputs. Zones 1, 2 and 3 are selected in a like manner. The output of zone gate 96 presents a one to the interrupter gate 98 upon the identification of a zone having four associated control flip-flops set. Initially, inputs 100 and 102 of gate 98 are high and a zero or ground state appears at input 104 of the look at me flip-flop 106. The output 108 of the flip-flop 106 is sent to the crate controller through buffers 110. A unijunction timer can also be employed to provide an interrupt signal following a delay of twenty seconds in the event a single interrupt is not acknowledged.

The controller receives the interrupt L from terminal 108 of FIG. 5 and indicates to the computer that a service request requires action. The controller then initiates the appropriate N command and proper sub-address A1, A2, A4 to the triangulation module which is received in area 112 of FIG. 5. Upon receipt of these commands, the Q response flip-flop 114 is set during the strobe S1 portion of the command operation. The Q response is returned to the controller as necessary inter-module hand shaking. When the N command is received by the triangulation module, a command accepted signal X is generated and returned to the controller to indicate the module is able to perform the required action. Simultaneously, the N command and the sub-address commands, $\overline{A1}$, $\overline{A2}$, $\overline{A4}$ send the appropriate address information to the data selectors 94 illustrated in FIG. 7 to read the counter outputs and transfer the readout data to the read buses R1 through R8. The data selectors transfer the readout data via data transfer lines M0 through M8. Read bus R9 and data transfer line M9 are used to give the indication of which zone has initiated the data readout. Typically, the computer would read all eight counters on a module following a look at me request with one of four zone numbers being indicated by bit R9 of the first four data transfers. During the strobe S2, portion of the command operation the response Q flip-flop 114 is reset. Also, the functional codes F1, $\overline{F2}$, $\overline{F4}$, F8, $\overline{F16}$ along with the N command and strobe S1 create a reset pulse to reset all zone flip-flops 116 through 122 and to assure reset of response Q flip-flop 114 as well as interrupt L flip-flop 106 illustrated in FIG. 5. The zone flip-flops are set when the corresponding counter control flip-flops 58 are set.

An additional feature of the triangulation module is the $\overline{HOLD}$ signal. When four counters associated with the zone begin counting, the output of zone gate 96 goes to zero and is applied through two inverters and gate 124 to delay gate 126 illustrated in FIG. 5. Gate 126 delays the $\overline{HOLD}$ signal sufficiently long to insure that the zone flip-flops 116 through 122 get set before the $\overline{HOLD}$ resets the counter control flip-flops 58. The $\overline{HOLD}$ signals locks all eight counters on the module in their respective states. After the computer has read the counters, it sends a reset signal which resets the zone flip-flops and releases the $\overline{HOLD}$ signal. An output $HOLD_{N+1}$ is fed to terminal 128 and optionally can be tied to the $HOLD_{N-1}$ input 130 of the next successive triangulation module. Similarly, the $HOLD_{N+1}$ signal from a previous module can be fed to terminal 130 of the module illustrated. This allows interlocking zones not only on a module but also those on other modules to avoid multiple recognitions of acoustic burst. When $\overline{HOLD}$ is zero, the $HOLD_{N+1}$ is a one which generates a $\overline{HOLD}$ in the next module to lock out incoming pulses. Furthermore, the output from terminal 88 is connected to the counter circuits 90 at like terminals 88 to prevent resetting of the counter for the duration of the $\overline{HOLD}$ output. Accordingly, the system can be expanded to handle an infinite number of zones without affecting the interplay between zones that avoids multiple recognitions of acoustic bursts.

In some instances, four transducers are available to form a zone area. In other situations, only three transducers are available for covering a zone area. While the triangulation module is suitable for monitoring eight sensors and four zones as would be the application on a cylindrical shape, it can be appreciated by those skilled in the art that the system is versatile enough to also service zones where only three sensors are used.

Thus, the system and methods of this invention enable the surveillance of relatively large component surfaces requiring a large number of sensors, while utilizing a minimum of equipment to provide reliable and accurate information on the source location of acoustic emissions.

We claim as our invention:

1. Apparatus for monitoring the presence and source location of acoustic emissions generated within or on an acoustically conductive medium segregated into a plurality of quadrilateral monitoring zones comprising:

a first group of four acoustic transducers respectively adapted to be acoustically coupled at corresponding corners of a first of the monitoring zones on the acoustically conductive medium in a manner to monitor acoustic emissions communicated to the transducer coupling locations, the respective transducers being responsive to the reception of an acoustic emission to provide a corresponding electrical output;

a second group of four acoustic transducers respectively adapted to be acoustically coupled at corresponding corners of a second monitoring zone adjacent the first monitoring zone in a manner to monitor acoustic emissions communicated to the coupling locations of the transducers of the second group, the transducers of the second group being responsive to the reception of an acoustic emission to provide a corresponding electrical output, and wherein the first and second zones have at least one common corner and the first and second groups share the transducer coupled to the common corner;

a plurality of electrical counters corresponding to the number of transducers respectively connected to a corresponding one of the transducers and individually responsive to an output of the corresponding transducer representative of an acoustic reception to sequence through the states of the counter;

means for identifying the group of transducers first encountering an acoustic reception on all four transducers within the group; and means for reading the counter states on the respective counters corresponding to the transducers within the identified group so that the difference in reception time of the acoustic emission at the coupling locations of the four transducers within the identified group can be interpreted.

2. The apparatus of claim 1 wherein the first and second zones have two common corners and the first and second groups of transducers share the transducers coupled to the common corners.

3. The apparatus of claim 1 including means responsive to the identifying means to inhibit the counters corresponding to the transducers within the identified group from further sequencing through the counter states and maintain the last state sequenced upon identification of the group of transducers first encountering an acoustic reception on all four transducers.

4. The apparatus of claim 3 wherein the inhibiting means prevents the counter corresponding to the last transducer within the identified group that encounters an acoustic reception from sequencing past the zero counter state.

5. The apparatus of claim 3 wherein the inhibiting means prevents all of the counters from further sequencing through the counter states upon identification of the group of transducers first encountering an acoustic reception on all four transducers.

6. The apparatus of claim 5 wherein the first and second groups of transducers, the counters, the identifying means, the reading means and the inhibiting means comprise a module further including an interlock operable to couple the inhibit means to like interlocks on n additional modules, where n is an integer which can vary between one and infinity, in a manner that renders the respective inhibiting means responsive to the identifying means on the n+1 modules to inhibit all of the counters from further sequencing through their respective counter states upon the identification of the group of transducers first encountering an acoustic reception on all four transducers.

7. The apparatus of claim 3 including means for deactivating the inhibiting means from preventing the counters to sequence.

8. The apparatus of claim 1 includng a plurality of monitoring means corresponding to the plurality of counters and respectively responsive to a given output state of a corresponding one of the counters to stop the counters from further sequencing until the occurrence of the next corresponding transducer output.

9. The apparatus of claim 8 wherein the given output state corresponds to the time required for an acoustic emission to travel within the acoustically conductive medium between the two furtherest spaced corners of a monitoring zone.

10. The apparatus of claim 1 wherein the output of the respective transducers are electrically coupled to the corresponding counters in a manner to reset the counters upon the initiation of the transducer output.

11. A method of monitoring the presence and source location of acoustic emissions generated within or on an acoustically conductive medium comprising the steps of:

segregating a surface of the medium into a plurality of quadrilateral monitoring zones;

monitoring acoustic emissions communicated to the respective corners of the respective zones;

generating corresponding electrical signals representative of the acoustic emissions monitored;

employing the electrical signals to enable corresponding counters to sequence through the counters respective counting states;

identifying the zone first encountering an acoustic reception at all its corresponding monitoring locations; and reading the states of the counters corresponding to the identified zone.

12. The method of claim 11 wherein the segregating step divides the medium into adjacent zones sharing two common corners.

13. The method of claim 11 including the steps of inhibiting the counters corresponding to the identified zone from further sequencing through the counter states and maintaining the last state sequenced upon identification of the zone.

14. The method of claim 13 wherein the inhibiting step prevents the counter corresponding to the electrical signal representative of the last acoustic reception monitored within the identified zone from sequencing past the zero counter state.

15. The method of claim 13 wherein the inhibiting step prevents all the counters from further sequencing through the counter states once a zone is identified.

16. The method of claim 11 including the steps of:
monitoring the counters for the occurrence of a given output state; and
stopping the respective counters exhibiting the predetermined output state from further sequencing until the occurrence of the next corresponding electrical signal.

17. The method of claim 16 wherein the given output state corresponds to the time required for an acoustic emission to travel within the acoustically conductive medium between the two furtherest spaced corners of a monitoring zone.

18. The method of claim 16 including the step of resetting the counters upon the initiation of the corresponding electrical signal.

19. The method of claim 11 for monitoring acoustic emissions generated within or on an acoustically conductive medium having a generally circular circumference in at least one dimension wherein the segregating step divides the circumference in the one dimension into a plurality of zones around the entire girth of the circumference sharing each monitored location with two adjacent zones.

* * * * *